United States Patent [19]

McCaffrey

[11] Patent Number: 4,647,201

[45] Date of Patent: Mar. 3, 1987

[54] ATOMIC ABSORPTION SPECTROPHOTOMETER WITH IMPROVED DRAIN TRAP INTERLOCK

[75] Inventor: John T. McCaffrey, Hamden, Conn.

[73] Assignee: The Perkin-Elmer Corporation, Norwalk, Conn.

[21] Appl. No.: 818,453

[22] Filed: Jan. 13, 1986

[51] Int. Cl.$^4$ .................................. G01N 21/72
[52] U.S. Cl. ..................... 356/315; 356/417; 431/33; 431/126; 431/346
[58] Field of Search ................ 356/315, 417; 431/4, 431/33, 126, 346

[56] References Cited

U.S. PATENT DOCUMENTS

| | | | |
|---|---|---|---|
| 4,367,042 | 1/1983 | Smith, Jr. et al. | 356/315 |
| 4,568,267 | 2/1986 | Kendall-Tobias | 356/315 |
| 4,606,718 | 8/1986 | Kendall-Tobias | 356/315 |

Primary Examiner—F. L. Evans
Attorney, Agent, or Firm—Edwin T. Grimes; F. L. Masselle

[57] ABSTRACT

The interlock assures that the end of a drain trap entrance pipe is covered with liquid. The system includes a control circuit with a circuit element which changes impedance with temperature changes. The circuit element is arranged to be thermally coupled with the drain trap liquid when the discharge end of the drain trap entrance pipe is immersed in the liquid. The circuit applies a current to the circuit element to thereby apply energy thereto. The circuit element achieves a lower steady-state temperature when thermally coupled with the liquid. The control circuit is operable to detect the difference in resistance when the circuit element is at the lower temperature. The control circuit is connected to a valve device for controlling combustion gas for the spectrophotometer and is operable to enable the valve device to enable the spectrophotometer when the circuit element is at the lower temperature and to disable the spectrophotometer at a higher temperature.

13 Claims, 2 Drawing Figures

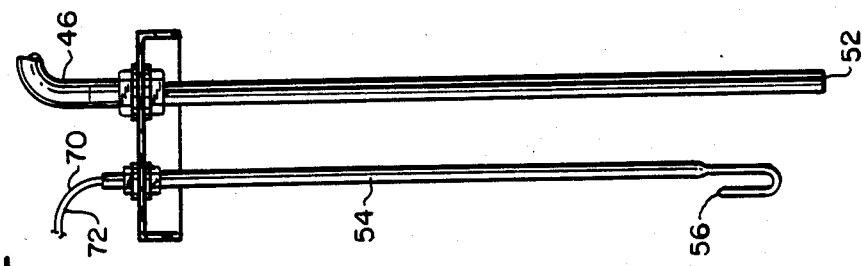
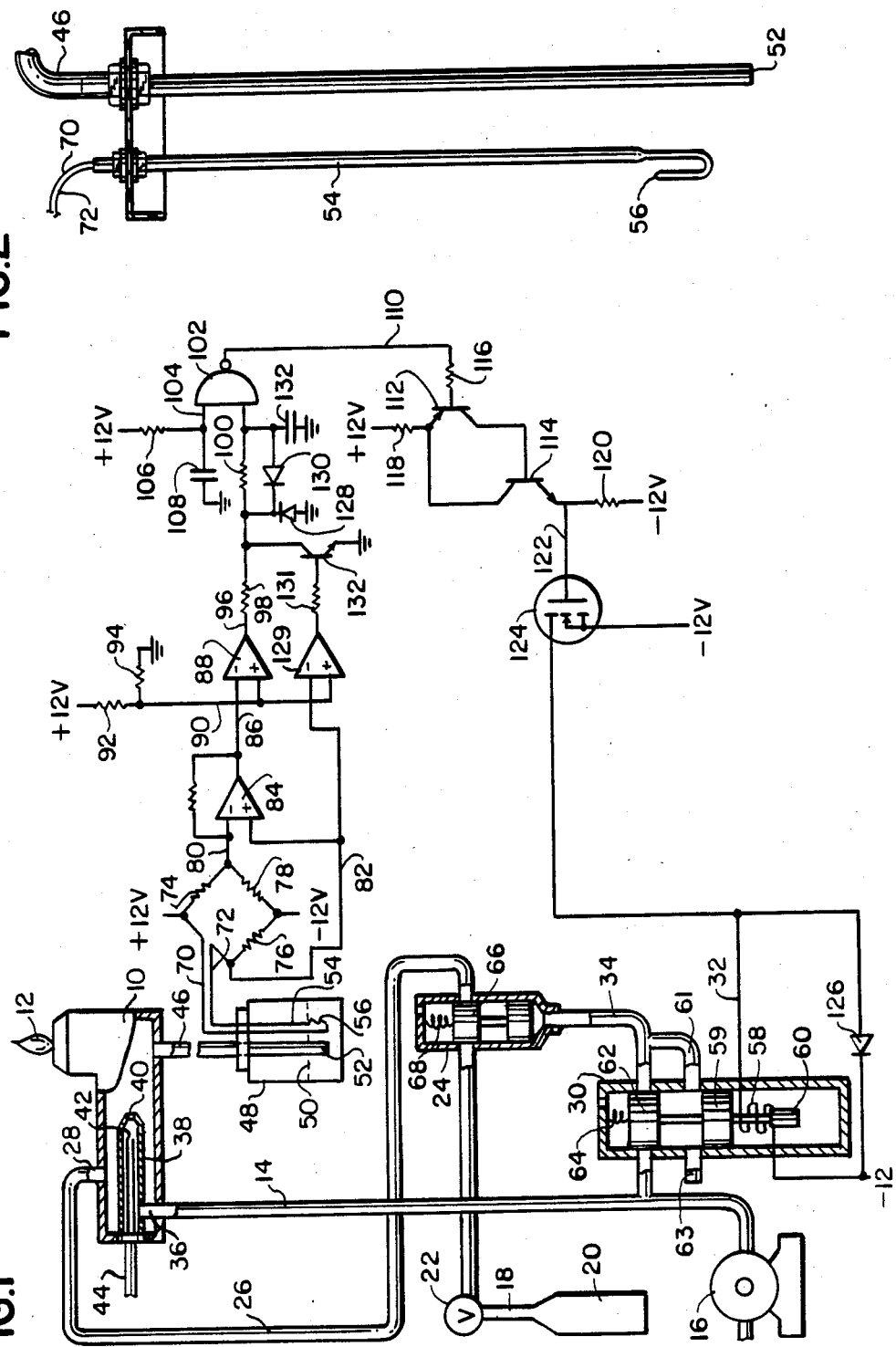

ATOMIC ABSORPTION SPECTROPHOTOMETER WITH IMPROVED DRAIN TRAP INTERLOCK

FIELD OF THE INVENTION

This invention relates generally to flame atomic absorption spectrophotometers, and particularly to burner apparatus for atomic absorption spectrophotometers provided with safety interlock means for improvement of the safety of operation.

BACKGROUND OF THE INVENTION

In atomic absorption spectroscopy, the measurement of the absorption of a radiation beam at a characteristic resonant spectral line for a particular element yields a measure of the concentration of that element in an original sample solution. Presently, one of the most common techniques for atomizing an element for purposes of the absorption measurement is by introducing a liquid sample solution of the element of interest into a gas burner wherein droplets of the solution are vaporized and the elements ultimately atomized, so as to form in the path of the apparatus radiation beam, a substantial quantity of the element of interest in its atomic state. A samle light beam, which originates from a line-emitting light source, and which includes a resonance line of the element to be measured, is directed through the flame. The desired element in the sample absorbs the resonance lines characteristic of the element and the emerging light beam is directed to a monochromator and thence to a detector which measures the degree to which the desired element absorbs the resonance lines of the sample beam. This absorption degree represents the amount of desired element in the sample substance.

For satisfactory operation of flame atomic absorption spectrophotometers, it is usually necessary to employ highly combustible mixtures of gases, such as mixtures of acetylene gas with an oxidant such as air or nitrous oxide.

In order to assure a quiet flame, the preferred practice is to supply an excess of the liquid sample solution over the amount which can be vaporized in order that larger droplets, which would result in a noisy flame, can be discarded. This excess of the sample solution must be drained away safely so that the burner does not become flooded with the excess liquid sample solution.

One of the potential hazards in the operation of such a system is that the combustible mixture of gases may accumulate in a liquid drain trap which is connected to receive the excess of the liquid sample solution which is drained from the burner, and that the accumulated gases in the liquid drain trap may later explode.

In order to avoid this occurrence, it is important that the end of the liquid drain line which carries excess solvent into the drain trap must be covered with liquid in the drain trap container so as to thereby restrict the flow of the explosive mixture of gases from the burner into the drain trap container.

Previously, it has been necessary to rely upon the operator to be sure that the liquid level in the drain trap is high enough to cover the lower end of the drain line, or to provide a float switch interlock to shut the system down if the liquid goes below a level which will cover the lower end of the drain line. However, both arrangements have shortcomings. Relying upon the operator is generally not considered safe, and the float switch arrangement has been found to be expensive, and may not be as reliable as desired.

Accordingly, it is an important object of the present invention to provide an atomic absorption spectrophotometer having an improved drain trap interlock which is lower in cost than prior interlocks.

It is another important object of the present invention to provide an atomic absorption spectrophotometer having an improved drain trap interlock which is more reliable than prior interlocks.

Further objects and advantages will be apparent from the following description and the accompanying drawings.

SUMMARY OF THE INVENTION

In carrying out the invention there is provided an atomic absorption spectrophotometer system comprising a flame atomic absorption spectrophotometer burner and apparatus for delivery of a fuel gas and at least one oxidant gas to said burner and a drain and a drain trap for draining excess sample solvent from said burner, said system including an improved interlock for said drain trap for assuring that the discharge end of a drain trap entrance pipe into said drain trap is covered with liquid to avoid the accumulation of combustible gases in said drain trap, comprising a control circuit including an electrical circuit element which changes impedance with temperature changes, said circuit element being arranged to be thermally coupled with the drain trap liquid when the discharge end of the drain trap entrance pipe is immersed in the liquid, said control circuit including means for applying an electrical current to said circuit element to thereby apply energy thereto, said circuit element being operable to achieve a lower steady-state temperature when thermally coupled with the liquid by energy dissipation in the liquid and to achieve a higher steady-state temperature when thermally coupled only with a gas, a valve means for controlling the flow of at least one gas to said atomic absorption spectrophotometer system, means for connecting said control circuit to said valve means, said control circuit being operable to detect the difference in resistance when said circuit element is at the lower temperature and to then control the operation of said valve means to enable said system, and said control circuit being operable to detect the difference in resistance when said circuit element is at the higher temperature and to then control the operation of said valve means to disable said system.

DETAILED DESCRIPTION OF THE DRAWINGS

FIG. 1 is a schematic diagram of an apparatus for carrying out the present invention.

FIG. 2 is a mechanical detail view showing a preferred embodiment of an electrical probe component of the improved drain trap interlock of the present invention.

DESCRIPTION OF PREFERRED EMBODIMENTS

Referring particularly to FIG. 1, there is illustrated a burner 10 for a flame atomic absorption spectrophotometer, with the flame being illustrated at 12. In a typical arrangement, the apparatus includes a conduit 14 for conveying compressed air from a source such as an air compressor 16, and a fuel conduit 26 connected to receive fuel such as acetylene gas, from a pressurized canister 20. The fuel is supplied to the burner 10 through a control valve 22, a shutoff valve 24, the conduit 26, and a burner port 28. The system may include arrangements (not shown) for changing the oxidant from air to nitrous oxide. A system of that kind is illustrated in a co-pending U.S. patent application, Ser. No. 670,712, now U.S. Pat. No. 4,606,718 entitled "Method and Apparatus for Shutting Down the Burner of a Flame Atomic Absorption Spectrophotometer" and filed by Michael Kendall-Tobias on Nov. 13, 1984 and assigned to the same assignee as the present application.

The present system, as illustrated, is arranged so that acetylene gas is supplied to the burner 10 through the control valve 24 only when there is sufficient oxidant (air) pressure available in the conduit 14, and only when an electromagnetically controlled valve 30 is energized by an electrical signal at 32 to connect oxidant (air) pressure through a control conduit 34 to the control valve 24. This safety interlock arrangement, which permits the flow of acetylene gas to the burner 10 only when there is a sufficient oxidant gas pressure available, through the operation of the control valve 24, forms a part of the subject matter disclosed and claimed in a previously filed and co-pending U.S. patent application Ser. No. 670,711, now U.S. Pat. No. 4,571,172, entitled "Safety Apparatus for an Atomic Absorption Spectrophotometer Burner" filed by Michael Kendall-Tobias on Nov. 13, 1984 and assigned to the same assignee as the present application.

The oxidant is supplied through the conduit 14, and through a port 36 to a nebulizer 38 which forms a part of the burner 10. The nebulizer 38 includes a nozzle 40 and an aspirator tube 42 through which a liquid sample including material to be analyzed is supplied through an inlet pipe 44. The excess of the liquid sample flows by gravity to the bottom of the burner housing 10, and flows through a drain tube 46 and thus into a drain trap container 48 where it accumulates to a liquid level indicated at 50. The drain line terminates in a rigid tube 52 the lower end of which extends down beneath the level 50 of the liquid.

If there is insufficient liquid in the drain trap container 48 to cover the lower end of the drain line tube 52, then the combustible gases from the burner 10 can accumulate in the drain trap container 48 and cause an explosion.

In accordance with the present invention, in order to assure that the liquid level 50 is above the lower end of the drain tube 52, a probe 54 containing a circuit element device 56 is provided to be thermally coupled with the liquid when the end of the drain pipe 52 is immersed in the liquid. The thermal coupling is preferably achieved by immersion of the probe in the liquid. The circuit element is designed to change impedance with temperature changes, and the associated circuit is designed to apply energy to the element 56 which raises the temperature of the element 56 to a greater extent if the element 56 is not thermally coupled with liquid, and to a lesser extent if the element is thermally coupled with liquid. An electrical measurement of the impedance of the element 56 is made, and that measurement is used to control the operation of the electromagnetically actuated control valve 30 to prevent operation of the system if the liquid level 50 is below the end of the drain pipe 52.

The circuit element 56 is preferably a thermistor device which has a negative temperature resistance characteristic. That is, the resistance goes down as the temperature goes up. Device 56 is sometimes referred to below as a variable resistance device.

The electromagnetic valve 30 is shown schematically as including a winding 58 which operates on a solenoid core 60 to move a piston which includes an upper piston land 62 against the force of a return spring 64. In its raised position, when the winding 58 is energized, the piston land 62 opens the associated ports to permit the pressure from the oxidant line 14 to be delivered to the conduit 34 to actuate the control valve 24. At the same time, a lower piston land 59 closes a connection 61 from conduit 34 to a discharge port 63. When the solenoid valve winding 58 is de-energized, the ports at land 62 are closed, and the conduit 34 is vented at land 59 through vent port 63.

Valve 24 includes a piston having an upper land 66 which is moved upwardly by the oxidant pressure in conduit 34 to uncover the ports associated with the acetylene conduit line 26 to permit the delivery of acetylene gas to the burner 10. The upward movement of the piston 66 is opposed by a return spring 68.

The circuit connected between the variable resistance device 56 and the input connection 32 of the solenoid valve 30 is described in detail below.

The variable resistance device 56 is connected in a bridge circuit arrangement by means of conductors 70 and 72. The bridge circuit arrangement includes resistors 74, 76, and 78. The top of the bridge is supplied with +12 volts dc and the bottom of the bridge is supplied with −12 volts dc from a supply source, not shown. The voltages applied to the bridge cause currents in the elements of the bridge, including a current through the variable resistance device 56. That current, in a preferred embodiment of the invention, provides about 30 milliwatts of power to the resistor device 56. If the resistor device 56 is in air because the level 50 of the liquid in the liquid trap container 48 is not sufficiently high to cover the resistor device 56, then the temperature of the device 56 rises substantially more than it would if covered with liquid. The rise in temperature when the device is in air causes the impedance of the device to be substantially reduced. Under these circumstances, the bridge is substantially balanced, and the outputs from the bridge at connections 80 and 82 are both approximately 5.5 volts.

However, if the device 56 is covered with liquid, by reason of a proper level 50 of the liquid in the container 48, then the temperature of the device 56 goes down, the resistance of the device 56 goes up, and the bridge is unbalanced. This reduces the potential at connection 82 to about 1.4 volts. The resultant difference of about 4.1 volts at connections 80 and 82 energizes a comparator amplifier 84 to provide an output voltage at connection 86 of about −9 volts. This −9 volt signal is supplied to the inverting input of a comparator amplifier 88. The noninverting input of amplifier 88 is supplied with an input voltage of about −6 volts at connection 90 from a voltage divider including resistors 92 and 94 which is supplied with a −12 volt supply voltage.

The resultant voltage difference at the inputs of comparator amplifier 88 results in an output voltage at connection 96 of about 10 volts. This voltage is supplied through a resistor 98 and a resistor 100 to provide a logic 1 input to a NAND gate 102. Under steady-state operating conditions, NAND gate 102 also receives a logic 1 input at connection 104 from a circuit including resistor 106 and capacitor 108. These two logic 1 inputs to NAND gate 102 result in a logic 0 output at connection 110 which is supplied to a Darlington transistor circuit including transistors 112 and 114, and resistors 116, 118, and 120.

The logic 0 input is inverted by the Darlington circuit and supplied at an output connection 122 to the control electrode of a field effect transistor 124 which, in response to the signal from the Darlington circuit, energizes the solenoid valve 30 through connection 32. A "freewheeling" diode 126 is preferably provided around the winding 58 of the solenoid valve in order to assist in commutation of the winding current whenever the field effect transistor 124 is deenergized. Diode 126 is back biased whenever the field effect transistor 124 is energized.

Referring back again to the bridge in which the thermistor 56 is connected, as previously stated, when the thermistor 56 is in air, the bridge is balanced so that the voltages at connections 80 and 82 are both approximately 5.5 volts. With these equal voltages on the comparator amplifier 84 inputs, the output at connection 86 is approximately zero. The combination of the resulting zero input at the noninverting input connection 86 of comparator amplifier 88 together with the −6 volt input at the noninverting input of that amplifier results in a −10 volt output at connection 96. This negative voltage forward biases both of the diodes 128 and 130. Diode 130 shorts out the resistance 100, and diode 128 clamps the associated input to AND gate 102 to ground, thus providing a logic 0 input to NAND gate 28. In the previously described operation, where the output at 96 was positive, the diodes 128 and 130 were both back biased, so that they did not influence the operation of the circuit.

Continuing with the present description, the logic 0 at the lower input of NAND gate 102 assures that there is a logic 1 output at connection 110 to the Darlington circuit including transistors 112 and 114. After inversion of the signal by the Darlington circuit, the output at connection 122 to the field effect transistor 124 is a logic 0, so that the field effect transistor 124 is not switched on, and the solenoid valve 30 is not energized. Thus, the system is not supplied with acetylene gas if the liquid level in the trap container 48 is low enough to uncover the lower end of the drain tube 52.

Referring back again to the NAND gate 102, a capacitor 132 is preferably connected between the lower input of NAND gate 102 and ground. Capacitor 132 operates, together with the resistors 98 and 100, to provide a brief time delay, preferably in the order of three seconds, when a positive voltage signal appears at connection 96 as the result of cooling of the resistor device 56. This three second delay guards against a false start-up of the apparatus due to a momentary cooling of the thermistor device 56 which may result from splashing of the solvent liquid within the trap 48.

When the apparatus is initially started up, if the solvent level 50 is not high enough, so that the thermistor 56 is in air, a false signal might be given to the system initially by reason of the fact that the thermistor has not yet had time to reach the operating temperature indicating the low liquid level. The circuit at the upper input 104 of the NAND gate 102 initially delays the operation of the system to accommodate for this problem. Thus, the capacitor 108 initially holds the upper input 104 of NAND gate 102 at a logic 0. After a time delay determined by the value of resistor 106 and the capacitor value of capacitor 108, capacitor 108 charges up sufficiently to provide a voltage at 104 which is recognized by the NAND gate 102 as a logic 1. In this manner, the operation of the circuit is initially held off until the thermistor has time to achieve the elevated operating temperature if it is in air. In a practical embodiment, a suitable delay has been found to be about twenty seconds.

If the thermistor 56, or the circuit for the impedance device 56, develops an open circuit condition, then it appears to the remainder of the circuit that the impedance of the device has increased from immersion of the device in the liquid solution, even though the liquid level may be too low. To guard against this problem, another comparison amplifier 129 is provided which responds to the open circuit condition of the thermistor 56 circuit. Under the open thermistor circuit condition, the voltage at connection 82 is essentially −12 volts, and that voltage is applied to the inverting input of comparison amplifier 129. The −6 volts from conductor 90 is applied to the noninverting input of that comparison amplifier. The combination of these two voltages provides a positive voltage output from amplifier 129 which is supplied through resistor 131 to the base of transistor 132, turning on that transistor to clamp the lower input of NAND gate 102 to ground. This provides a logic 0 input to NAND gate 102, assuring that the associated circuit does not energize the solenoid valve 30. Thus, the system cannot be operated if the liquid level sensing function of the thermistor 56 is inoperative because of an open circuit.

The function of the NAND gate 102 is preferably fulfilled by means of a Schmitt trigger circuit, which provides a precise switching function.

While the precise circuit disclosed and described above represents the preferred circuit for the present invention, it will be apparent that various changes and modifications may be made. For instance, the bridge in which the thermistor 56 is connected may be designed to be balanced when the thermistor is in liquid, and unbalanced when the thermistor is in air. This is the sense opposite to the sense of the operation just described for the circuit. The remainder of the circuit is then designed to energize the solenoid valve 30 only when the bridge is balanced.

Flame atomic absorption spectrophotometers are often used with air as the start-up oxidant, and nitrous oxide as the oxidant used in continuing operations. In such a system, the control valve 24 may be operated, and maintained open, through the solenoid valve 30 by means of the oxidant pressure which consists of either air or nitrous oxide.

An additional advantage of the system as disclosed is that any general failure of the electrical system will result in the loss of power to the winding of the solenoid valve 30, causing the system to shut down. Thus, the system is "fail-safe".

The arrangement of the valves and gas lines illustrated in the drawing is the preferred arrangement. However, it will be understood that various other arrangements may be employed in accordance with the present invention, as long as the basic objective of providing a solenoid valve which controls the operation of the burner is achieved. For instance, the solenoid valve 30 can be placed directly in series in the gas supply line 26, instead of the arrangement as shown. Furthermore, the solenoid valve 30 may be arranged in a more elaborate gas supply system such as that shown in the previously-mentioned co-pending patent application, Ser. No. 670,712. That patent application discloses a system for shutting down a flame atomic absorption spectrophotometer burner by flooding the burner with nitrous oxide, the oxidant then being used in the burner.

FIG. 2 is a detail view showing the cover of drain trap container 48 together with the drain tube 52 and the probe 54. As shown in FIG. 2, the bottom end of the probe 54 is preferably formed and shaped to resemble a hook, and the thermistor 56 is mounted and positioned on the upwardly formed tip of the hook portion of the probe. This arrangement has the advantage that the thermistor is physically separated from any drops of solution which may be retained upon the probe immediately after the solution descends below the discharge end of the drain trap entrance pipe 52. The amount of energy supplied to the thermistor is so small that even a large drop of solution which is thermally coupled to the thermistor may keep the thermistor temperature down to falsely indicate that the thermistor is still submerged in liquid.

The probe 54 preferably consists of a stainless steel tube through which the wires 70 and 72 pass to the thermistor 56. The thermistor 56 is contained within a small bead of glass which is cemented, or otherwise securely attached, at the tip of the probe 54.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

What is claimed is:

1. An atomic absorption spectrophotometer system comprising a flame atomic absorption spectrophotometer burner and apparatus for delivery of a fuel gas and at least one oxidant gas to said burner and a drain and a drain trap for draining excess sample solvent from said burner, said system including an improved interlock for said drain trap for assuring that the discharge end of a drain trap entrance pipe into said drain trap is covered with liquid to avoid the accumulation of combustible gases in said drain trap, comprising a control circuit including an electrical circuit element which changes impedance with temperature changes, said circuit element being arranged to be thermally coupled with the drain trap liquid when the discharge end of the drain trap entrance pipe is immersed in the liquid, said control circuit including means for applying an electrical current to said circuit element to thereby apply energy thereto, said circuit element being operable to achieve a lower steady-state temperature when thermally coupled with the liquid by energy dissipation in the liquid and to achieve a higher steady-state temperature when thermally coupled only with a gas, a valve means for controlling the flow of at least one gas to said atomic absorption spectrophotometer system, means for connecting said control circuit to said valve means, said control circuit being operable to detect the difference in resistance when said circuit element is at the lower temperature and to then control the operation of said valve means to enable said system, and said control circuit being operable to detect the difference in resistance when said circuit element is at the higher temperature and to then control the operation of said valve means to disable said system.

2. A system as claimed in claim 1 wherein said control circuit includes a bridge circuit, said circuit element which changes impedance with temperature changes being connected in said bridge circuit as one of the arms of said bridge circuit, said bridge circuit being operable to be balanced at one steady-state temperature of said circuit element and to be unbalanced at a second steady-state temperature of said circuit element, one of said steady-state temperatures being achievable when said circuit element is thermally coupled with liquid, and the other one of said steady-state temperatures being achieved when said circuit element is thermally coupled only with a gas.

3. A system as claimed in claim 2 wherein said bridge circuit is balanced when said circuit element is thermally coupled only with a gas.

4. A system as claimed in claim 2 wherein said control circuit includes circuit means for detecting an open circuit condition in the circuit branch containing said circuit element which changes impedance with temperature changes, said means for detecting an open circuit condition being operable to control the operation of said control circuit and said valve means to disable said system.

5. A system as claimed in claim 2 wherein said control circuit includes at least one amplifier stage connected to said bridge circuit to determine whether or not said bridge circuit is balanced and to produce a logic 0 signal in response to a balanced bridge and a logic 1 signal in response to an unbalanced bridge, a NAND gate connected to receive said logic 1 and logic 0 signals, said NAND gate including a second input, a second input circuit for said NAND gate which is operable under steady-state conditions to provide a constant logic 1 input to said NAND gate, said NAND gate being operable to provide a logic 0 output in response to two logic 1 input signals resulting from an unbalanced bridge, a Darlington inverter circuit connected to receive said logic 0 signal output from said NAND gate and operable to produce a logic 1 output signal, a field effect transistor connected to receive said logic 1 signal and operable to become conductive in response to said logic 1 signal, said field effect transistor having an output circuit connected to control said valve means to enable said system in response to an unbalanced bridge.

6. A system as claimed in claim 1 wherein said valve means comprises a solenoid valve which is operable to be energized by said control circuit to enable said system by energization of said solenoid valve and to disable said system by de-energizing said solenoid valve.

7. A system as claimed in claim 6 wherein said solenoid valve is connected and arranged to control the delivery of fuel to said atomic absorption spectrophotometer burner.

8. A system as claimed in claim 7 which includes a fluid pressure operated control valve connected in a fuel line from a source of fuel to said burner to control the flow of fuel to said burner, and wherein said solenoid valve means is connected between the source of oxidant gas and said fluid pressure operated valve means to control the delivery of fuel by delivering pressurized oxidant gas to said fluid pressure operated valve to open said fluid pressure operated valve to deliver fuel to said burner.

9. A system as claimed in claim 1 wherein said electrical circuit element which changes impedance with temperature changes comprises a thermistor device.

10. A system as claimed in claim 9 wherein said thermistor is carried by a probe device which is arranged to extend downwardly into said drain trap, said probe device being shaped to resemble a hook at the lower end thereof, said thermistor device being mounted in the upwardly formed tip of said hook shape in said probe device so that said thermistor is physically separated from any drops of solution which may be retained upon said probe device immediately after the solution descends below the discharge end of said drain trap entrance pipe.

11. A system as claimed in claim 1 wherein said control circuit includes means for initially holding off the enablement of said valve means upon initial energization of said system in order to permit said circuit element to achieve a steady-state temperature indicating whether or not said circuit element is thermally coupled with liquid.

12. A system as claimed in claim 1 wherein said circuit includes circuit means for delaying the enablement of said system by said valve means in response to a lower temperature at said circuit element in order to compensate for momentary temperature reductions due to splashing of the solvent liquid upon said circuit element.

13. In an atomic absorption spectrophotometer system, an improved drain trap interlock for assuring that the end of a drain trap entrance pipe is covered with liquid, comprising a control circuit including an electrical circuit element which changes impedance with temperature changes, said circuit element being arranged to be thermally coupled with the drain trap liquid when the discharge end of the drain trap pipe is immersed in the liquid, said control circuit including means for applying an electrical current to said circuit element to supply energy thereto, said circuit element being operable to achieve a lower steady-state temperature when thermally coupled with the liquid and to achieve a higher temperature when thermally coupled only with a gas, a valve for controlling the flow of fuel to said atomic absorption system, means for connecting said control circuit to said valve, said control circuit being operable to detect the difference in resistance when said circuit element is at the higher temperature and to then close said valve to disable the system.

* * * * *